(12) United States Patent
Yasuhiro et al.

(10) Patent No.: US 10,098,604 B2
(45) Date of Patent: Oct. 16, 2018

(54) MEDICAL IMAGE PROCESSING DEVICE, MEDICAL IMAGING DEVICE, MEDICAL IMAGE PROCESSING METHOD AND MEDICAL IMAGING METHOD

(71) Applicant: Ziosoft, Inc., Tokyo (JP)

(72) Inventors: Kenichiro Yasuhiro, Tokyo (JP); Shinichiro Seo, Tokyo (JP)

(73) Assignee: ZIOSOFT, INC., Tokyo (JP)

( * ) Notice: Subject to any disclaimer, the term of this patent is extended or adjusted under 35 U.S.C. 154(b) by 17 days.

(21) Appl. No.: 15/277,422

(22) Filed: Sep. 27, 2016

(65) Prior Publication Data

US 2017/0086771 A1  Mar. 30, 2017

(30) Foreign Application Priority Data

Sep. 28, 2015  (JP) ................................. 2015-190112

(51) Int. Cl.
*G06K 9/46* (2006.01)
*A61B 6/00* (2006.01)
(Continued)

(52) U.S. Cl.
CPC ........ *A61B 6/5288* (2013.01); *A61B 5/02028* (2013.01); *A61B 5/0402* (2013.01);
(Continued)

(58) Field of Classification Search
CPC . A61B 6/5288; A61B 6/5294; A61B 5/02028; A61B 5/02035; A61B 5/0205; A61B 5/0402; A61B 5/04021; A61B 5/04023; A61B 6/032; A61B 6/0327; A61B 6/463; A61B 6/461; A61B 6/462; A61B 6/467; A61B 6/466; A61B 6/486; A61B 6/487; A61B 6/503; A61B 6/504; A61B 6/505; A61B 6/506; A61B 6/507; A61B 6/508; A61B 6/501; A61B 6/502; A61B 6/5205; A61B 6/5211; A61B 6/5217;
(Continued)

(56) References Cited

U.S. PATENT DOCUMENTS

2005/0089224 A1* 4/2005 Aoki .................. G06K 9/00711
382/173
2009/0316970 A1* 12/2009 Kemper ............... G06K 9/6223
382/131

(Continued)

*Primary Examiner* — Vincent Rudolph
*Assistant Examiner* — Stephen Brinich
(74) *Attorney, Agent, or Firm* — Pearne & Gordon LLP

(57) ABSTRACT

A medical image processing device includes a port, a processor and a display. The port acquires a plurality of image data from a living body. The processor classifies the plurality of image dam to genes ate a plurality of image groups based OH a first time component. The first time component is defined by a first time interval among imaging times at which the plurality of image data are generated. The processor correlates each image data in one image groups with each image data in another image group, based on both an actual time and a time ratio of a second time component. The second time component is defined by a second time interval among the imaging times being shorter than the first time interval. The display displays images based on the plurality of image data based on the correlation of the image data in the image groups.

19 Claims, 10 Drawing Sheets

(51) Int. Cl.
*A61B 5/02* (2006.01)
*A61B 5/0402* (2006.01)
*A61B 6/03* (2006.01)
*G06K 9/52* (2006.01)
*G06K 9/62* (2006.01)
*G06T 7/00* (2017.01)
*G06T 11/60* (2006.01)
*A61B 5/00* (2006.01)

(52) U.S. Cl.
CPC .............. *A61B 6/032* (2013.01); *A61B 6/463* (2013.01); *A61B 6/466* (2013.01); *A61B 6/486* (2013.01); *A61B 6/503* (2013.01); *A61B 6/5205* (2013.01); *A61B 6/5217* (2013.01); *A61B 6/5264* (2013.01); *G06K 9/52* (2013.01); *G06K 9/6267* (2013.01); *G06T 7/0012* (2013.01); *G06T 7/0016* (2013.01); *G06T 11/60* (2013.01); *A61B 5/7285* (2013.01); *A61B 6/541* (2013.01); *G06T 2207/10081* (2013.01); *G06T 2207/30048* (2013.01)

(58) Field of Classification Search
CPC ... A61B 6/5223; A61B 6/5264; A61B 6/5267; A61B 6/5276; G06K 9/52; G06K 9/522; G06K 9/525; G06K 9/527; G06K 9/6267; G06K 11/06
USPC ........ 382/131–134, 152–154, 107, 236, 285; 348/439.1, 510, 512
See application file for complete search history.

(56) References Cited

U.S. PATENT DOCUMENTS

| | | |
|---|---|---|
| 2011/0075888 A1 | 3/2011 | Matsumoto |
| 2011/0224531 A1* | 9/2011 | Steiner ................ A61B 5/021 600/407 |
| 2012/0250973 A1* | 10/2012 | Nambu ................... A61B 6/12 382/132 |
| 2013/0077750 A1* | 3/2013 | Yabugami ............. A61B 6/504 378/62 |
| 2013/0231548 A1 | 9/2013 | Brown |
| 2016/0206190 A1* | 7/2016 | Reisman ............. A61B 3/0025 |

* cited by examiner

MEDICAL IMAGE PROCESSING DEVICE, MEDICAL IMAGING DEVICE, MEDICAL IMAGE PROCESSING METHOD AND MEDICAL IMAGING METHOD

CROSS-REFERENCE TO RELATED APPLICATION

This application claims priority based on Japanese Patent Application No 2015-190112, filed on Sep. 28, 2015, the entire contents of which are incorporated by reference herein.

BACKGROUND OF THE INVENTION

1. Field of the Invention

The present disclosure relates to a medical image processing device, a medical imaging device, a medical image processing method and a medical imaging method.

2. Related Art

In the related art, a tissue analysis system that analyzes a tissue in the body is known. The tissue analysis system acquires a signal from a tissue to be analyzed and transforms the signal into a tissue characteristic value. Then, the tissue analysis system derives a variation of one tissue characteristic with respect to other tissue characteristics and displays the differences on an output device (for example, see US 2013/0231548 A)

SUMMARY OF THE INVENTION

In the tissue analysis system described in US 2013/0231548 A, it was difficult to confirm a change of a tissue such as a heart, which is deformable in the short term, before and after treatment such as surgery. Accordingly, a doctor has difficulty in determining whether an operation of a tissue is improved by treatment using even the tissue analysis system.

The present disclosure in made in consideration of the above-mentioned circumstances and provides a medical image processing device, a medical imaging device, a medical image processing method, a medical imaging method, and a medical image processing program which can easily confirm a long-term change of an observation target which is deformable in the short term.

A medical image processing device of the present disclosure includes a port, a processor and a display. The port acquires a plurality of two-dimensional or three-dimensional image data from a living body. The processor classifies the plurality of image data to generate a plurality of image groups based on a first time component. The first time component is defined by a first time interval among imaging times at which the plurality of image data are generated. The processor correlates each image data in one image groups with each image data in another image group, based on both an actual time of a second time component and a time ratio of a second time component. The second time component is defined by a second time interval among the imaging times. The second time interval is shorter than the first time interval. The display displays images based on the plurality of image data based on the correlation of the image data in the image groups.

A medical imaging device of the present disclosure includes an imaging unit and a processor and generates a plurality of image data at a plurality of imaging times. The imaging times includes a first time component which is defined by a first time interval and a second time component which is defined by a second time interval being shorter than the first time interval. The processor determines, based on both an actual time of the second time component and a time ratio of the second time component, according to a plurality of two-dimensional or three-dimensional first image data of a living body, the second time component of the plurality of second image data in correlation with the second time component of the plurality of first image data. The imaging unit images an image of the living body and acquires imaging data at the imaging times including the determined second time component. The processor generates the plurality of two-dimensional or three-dimensional second image data based on the imaging data.

A medical image processing method of a medical image processing device of the present disclosure, includes: acquiring a plurality of two-dimensional or three-dimensional image data from a living body; classifying the plurality of image data to generate a plurality of image groups based on a first time component, the first time component being defined by a first time interval among imaging times at which the plurality of image data are generated; correlating each image data in one image groups with each image data in another image group, based on both an actual time of a second time component and a time ratio of a second time component, the second time component being defined by a second time interval among the imaging times, and the second time interval being shorter than the first time interval; and displacing images based on the plurality of image data based on the correlation of the image data in the image groups.

A medical imaging method of a medical imaging device of the present disclosure generates a plurality of image data at a plurality of imaging times. The imaging times includes a first time component which is defined by a first time interval and a second time component which is defined by a second time interval being shorter than the first time interval. The medical imaging method includes: determining, based on both an actual time of the second time component and a time ratio of the second time component, according to a plurality of two-dimensional or three-dimensional first image data of a living body, the second time component of the plurality of second image data in correlation with the second time component of the plurality of first image data: imaging the living body and acquiring imaging data at the imaging times including the determined second time component; and generating the plurality of two-dimensional or three-dimensional second image data based on the imaging data.

A non-transitory computer readable medium of the present disclosure stores program for causing a medical image processing device including a port, a processor and a display. The computer readable medium executes operations including: acquiring a plurality of two-dimensional or three-dimensional image data from, a living body; classifying the plurality of image data to generate a plurality of image groups based on a first time component, the first time component being defined by a first time interval among imaging times at which the plurality of image data are generated; correlating each image data in one image groups with each image data in another image group, based on both an actual time of a second time component and a time ratio of a second time component, the second time component being defined by a second time interval among the imaging times, and the second time interval being shorter than the first time interval; and displaying images based on the plurality of image data based on the correlation of the image data in the image groups.

A non-transitory computer readable medium of the present disclosure stores program for causing a medical imaging device which includes an imaging unit and a processor and generates a plurality of image data at a plurality of imaging times. The imaging times includes a first time component which is defined by a first time interval and a second time component which is defined by a second time interval being shorter than the first time interval. The computer readable medium executes operations including: determining, based on both an actual time of the second time component and a time ratio of the second time component, according to a plurality of two-dimensional or three-dimensional first image data of a living body, the second time component of the plurality of second image data in correlation with the second time component of the plurality of first image data; imaging the living body and acquiring imaging data at the imaging times including the determined second time component; and generating the plurality of two-dimensional or three-dimensional second image data based on the imaging data.

According to the present disclosure, it is possible to easily confirm a long-term change of an observation target which is deformable in the short term.

BRIEF DESCRIPTION OF THE INVENTION

DETAILED DESCRIPTION OF THE INVENTION

Figure 1:
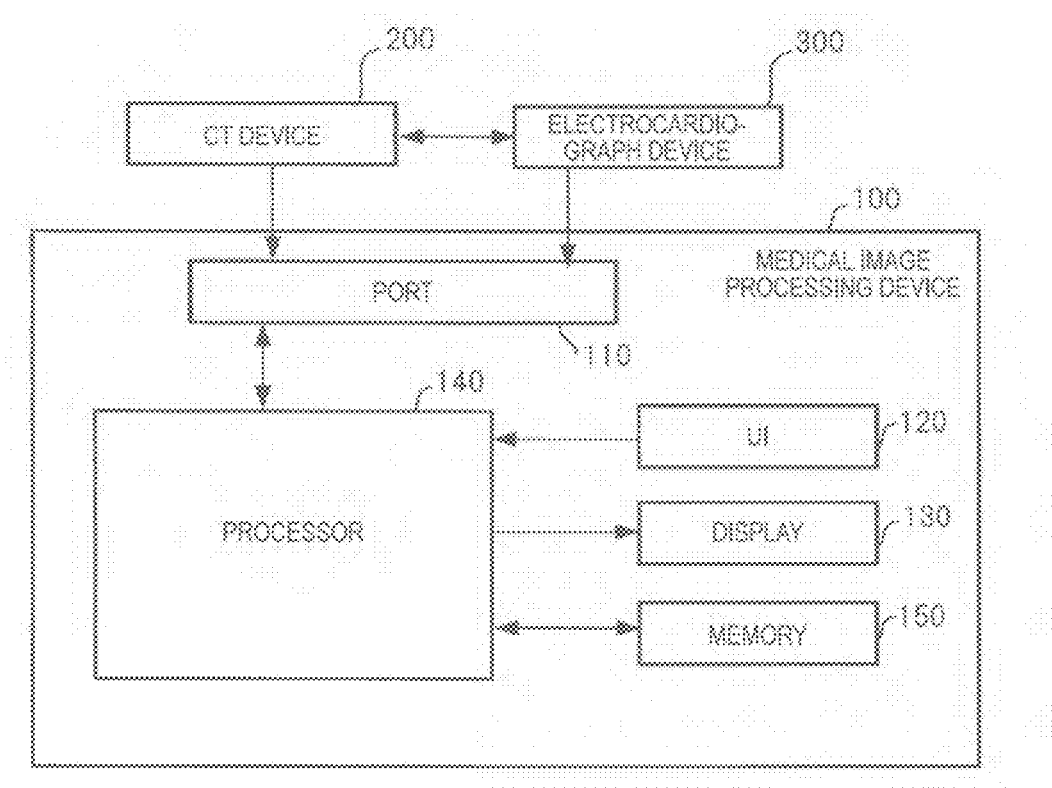
FIG. 1 is a block diagram illustrating a configuration example of a medical image processing device according to a first embodiment.

Hereinafter, embodiments of the present disclosure will be described with reference to the accompanying drawings.

History of Embodiments of the Present Disclosure

When a disease of an electrical conduction system of a heart is suspected, an electrocardiograph is mainly used to examine the heart. The electrocardiograph acquires electrocardiogram data. In the examination using the electrocardiograph, electrodes are attached to a patient, an electrical signal is acquired, and an electrical activity of the heart can be acquired in the form of a graph. Test results obtained using the electrocardiograph are used for diagnosis and treatment of the heart disease. The electrical activity of the heart can be understood using the electrocardiograph with a reduced load on a human body, but it cannot necessarily obtain all of the information required for diagnosis of a heart disease from the electrocardiogram.

When a complete examination is required by the examination using the electrocardiograph, an electrophysiology study (EPS) is carried out. In the EPS, an electrode catheter is inserted into an atrium or a ventricle, and a potential of an endocardium is measured or a reaction to an artificial electrical stimulation is acquired. Detailed information of a heart disease can be acquired by the EPS, but an invasion occurs in a human body and thus a risk of the patient increases.

When the heart disease is arrhythmia, the EPS can acquire information on whether a cause of tachycardia is a re-entry in which a loop occurs in an electrical transmission system or extrasystole in which a stimulation is generated from the outside of a sinoatrial node. When the heart disease is arrhythmia, the EPS can acquire information on whether a cause of bradycardia is a block in which the electrical transmission system is blocked or sinoatrial node dysfunction in which a stimulation is not generated from the sinoatrial node.

It is difficult to achieve both the ease of examination using the electrocardiogram and precision of examination using the EPS. When myocardial infarction occurs along with arrhythmia, detailed information of a lesion part could not be acquired from the electrocardiogram and thus the EPS and image diagnosis may be required.

In a similar manner to the electrical conduction system of the heart, it is preferable that a long-term change of a short-term deformable observation target other than the heart be easily confirmed.

A medical image processing device, a medical imaging device, a medical image processing method, a medical imaging method, and a medical image processing program will be described below which can easily confirm a long-term change of an observation target which is deformable in the short term.

In the present disclosure, a medical image processing device includes at least one port, at least one processor and at least one display. The port acquires a plurality of two-dimensional or three-dimensional image data from a living body. The processor classifies the plurality of image data acquired by the port to generate a plurality of image groups based on a first time component. The first time component is defined by a first time interval among imaging times at which the plurality of image data are generated. The processor correlates each image data in one image groups with each image data in another image group, based on both an actual time of a second time component and a time ratio of a second time component. The second time component is defined by a second time interval among the imaging times, and the second time interval is shorter than the first time interval. The display displays images based on the plurality of image data based on the correlation of the image data in the image groups correlated by the processor.

First Embodiment

Configuration of Medical Image Processing Device

FIG. 1 is a block diagram illustrating a configuration example of a medical image processing device 100 according to a first embodiment. The medical image processing device 100 includes a port 110, a user interface (UI) 120, a display 130, a processor 140, and a memory 150. A CT device 200 and an electrocardiograph 300 are connected to the medical image processing device 100. The medical image processing device 100 acquires volume data from the CT device 200 and processes the acquired volume data. The medical image processing device 100 may be constituted by a personal computer (PC) and software installed in the PC.

The CT device 200 irradiates a living body with X-rays and captures an image (CT image) using a difference in absorption of X-rays in a tissue in the body. The living body may include a human body. Plural CT images may be captured in a time-series manner. The CT image forms volume data including information of any position in the living body. Any position in the living body may include a heart. By capturing of the CT image, pixel values (CT values of pixels (voxels) in the CT image can be acquired. The CT device 200 transmits the volume data as the CT image to the medical image processing device 100 via a wired line or a wireless line.

The electrocardiograph 300 acquires the electrical activity of the heart as electrocardiogram data from the living body.

The port 110 acquires the volume data as the CT image. The acquired volume data may be immediately sent to the processor 140 and may be subjected to various types of processing therein, or may be stored in the memory 150 and then may be sent to the processor 140 and be subjected to various types of processing therein when necessary.

The port 110 may acquire electrocardiogram data from the electrocardiograph 300.

The UI 120 may include a touch panel, a pointing device, a keyboard, or a microphone. The UI 120 receives any input operation from a user of the medical image processing device 100. The user may include a doctor, a radiological technician, or a radiologist. The UI 120 may receive an operation of designating a predetermined region in the volume data. The predetermined region may include a heart.

The display 130 may include a liquid crystal display (LCD) and displays a variety of information. The variety of information includes a three-dimensional image which is acquired from the volume data. The three-dimensional image may include a volume rendering image, a surface tendering image, or a multi-planar reconstruction (MPR) image.

The memory 150 includes a read only memory (ROM), a random access memory (RAM), and the like. The memory 150 stores a variety of information and programs. The variety of information may include the volume data acquired by the port 110, images generated by the processor 140, and setting information set by the processor 140.

The processor 140 may include a central processing unit (CPU), a digital signal processor (DSP), or a graphics processing unit (GPU). The processor 140 performs various types of processing or control by executing a medical image processing program stored in the memory 150. The processor 140 controls each unit of the medical image processing device 100.

The processor 140 may extract a predetermined region from the volume data. In this case, the UI 120 receives designation of a region from the user and sends information of the region designation, to the processor 140. The processor 140 may extract the designated region from the volume data using a known method, based on the information of the region designation. The processor 140 may set a region through the user's manual operation instead of an input from the UI 120 and store the setting information in the memory 150.

The extracted region include a region of interest (ROI) which is noticed by the user. The extracted region may include a region of a heart.

Volume data of a predetermined region may the acquired by the CT device 200. The predetermined region may include a heart. In this case, the medical image processing device 100 may skip the process of extracting a predetermined region from the volume data.

The processor 140 generates a three-dimensional image based on the volume data acquired by the port 110. The processor 140 may generate a three-dimensional image from the volume data acquired by the port 110, based on the designated region.

Details of Heartbeat Phase

A heartbeat phase will be described below.

The CT device 200 acquires a plurality of three-dimensional volume data by continuously capturing an image. The plurality of three-dimensional volume data constitutes a moving image. Display of a moving image using the plurality of three-dimensional images is also referred to as four-dimensional (4D) display.

Figure 2:
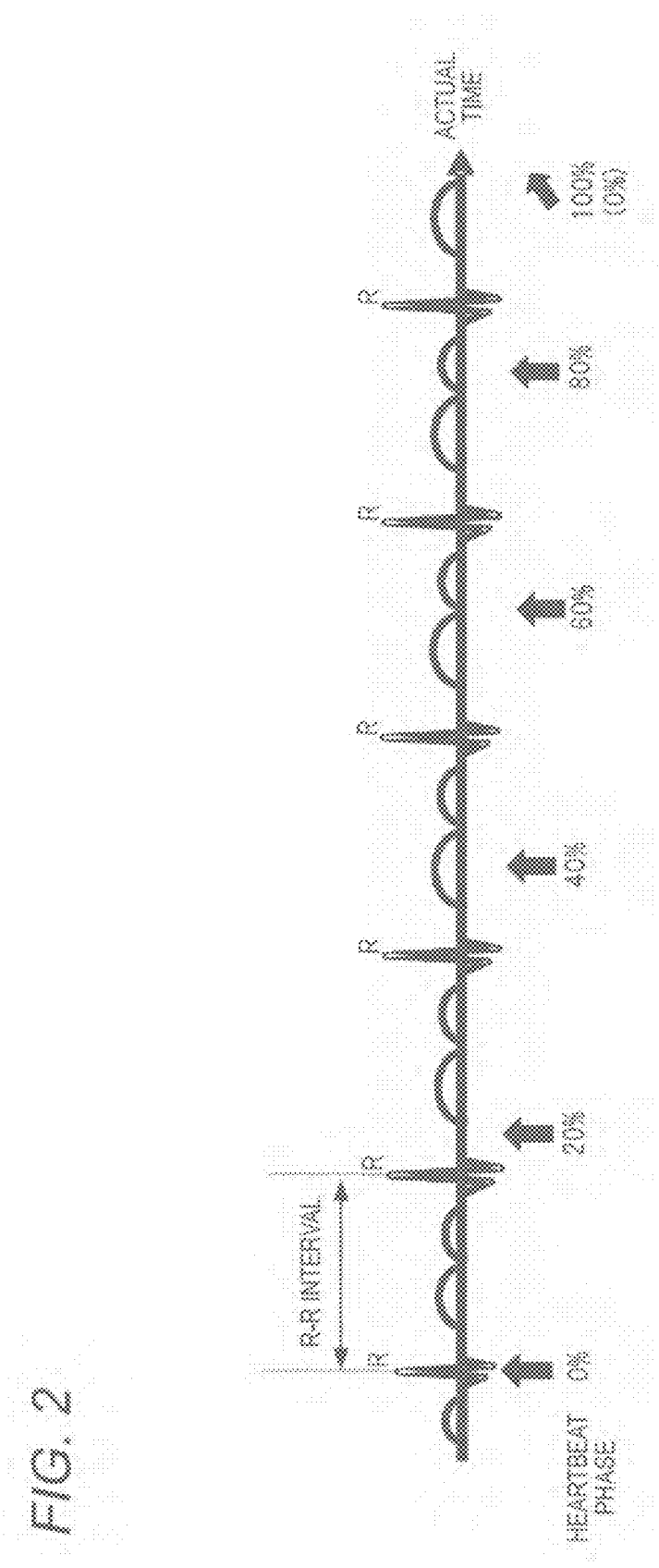
FIG. 2 is a schematic diagram illustrating an example of electrocardiogram data.
Figure 3:
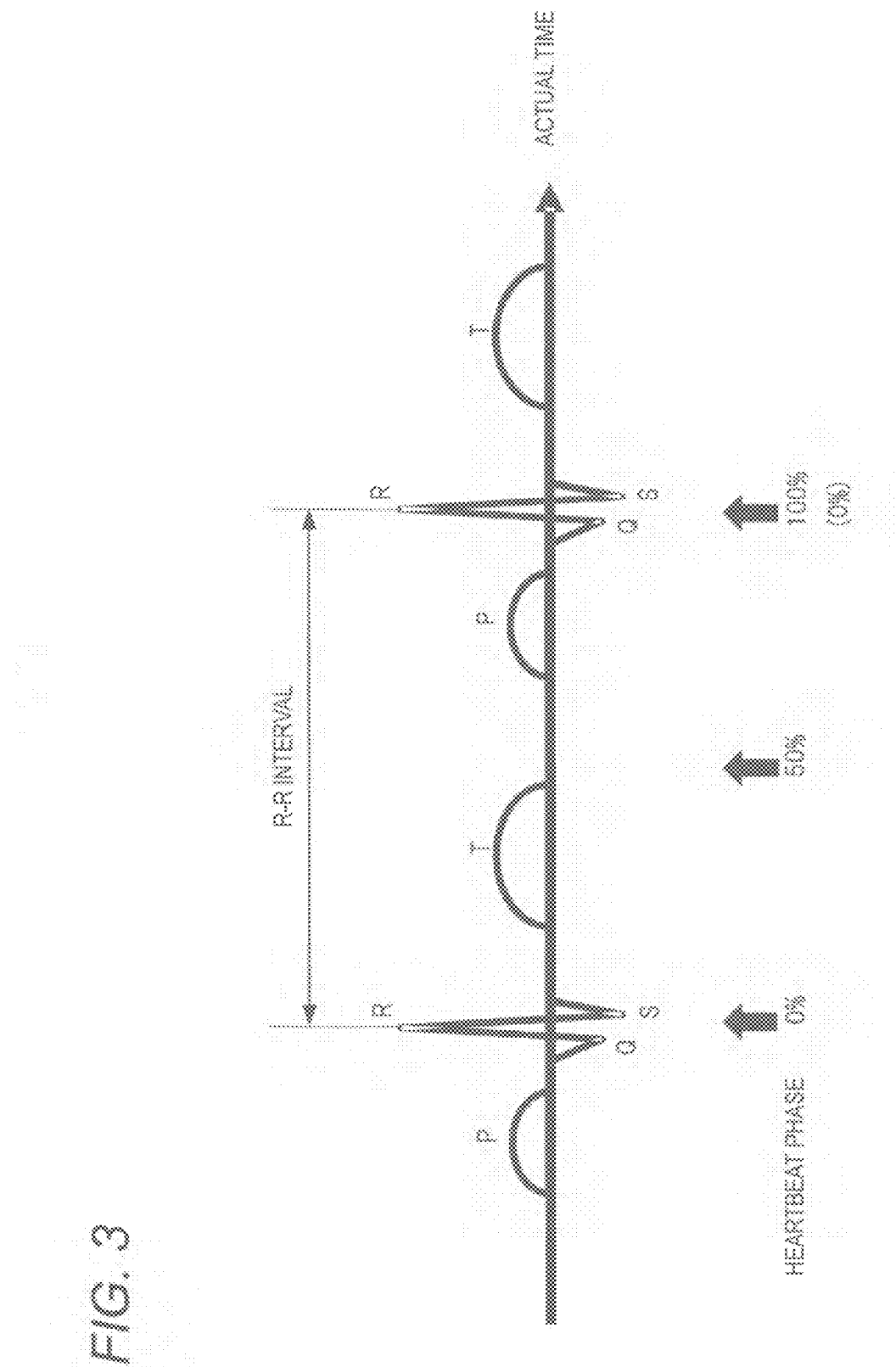
FIG. 3 is a zoomed view of the electrocardiogram, data illustrated in FIG. 2.
Figure 4:
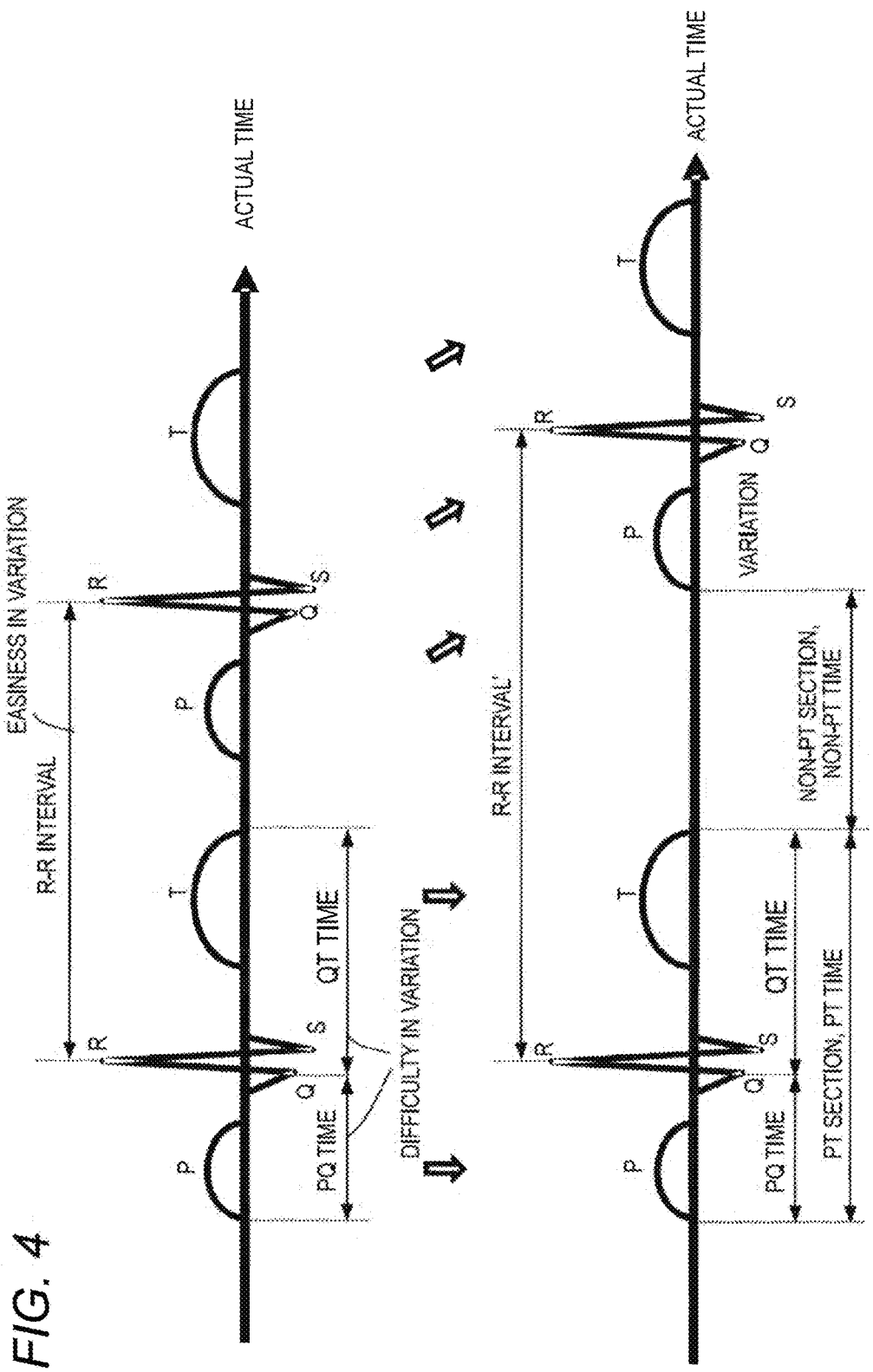
FIG. 4 is a schematic diagram illustrating an example of a plurality of electrocardiogram data having different cardiac cycles.

FIG. 2 is a schematic diagram illustrating an example of electrocardiogram data which is acquired by the electrocardiograph 300. FIG. 3 is a zoomed view of the electrocardiogram data illustrated in FIG. 2. FIG. 4 is a schematic diagram illustrating an example of a plurality of electrocardiogram data having different cardiac cycles. Here, the electrocardiogram data is illustrated in an electrocardiogram waveform.

As illustrated in FIGS. 2 and 3, since a heartbeat exhibits a periodic motion, the electrocardiogram waveform have a periodic change. The electrocardiogram waveform includes a P wave representing atrial contraction, a QRS complex representing ventricular contraction, and a T wave representing ventricular relaxation. Here, a time position in a cardiac cycle, that is, a ratio of a time to a cardiac cycle, is also referred to as a heartbeat phase. The heartbeat phase is expressed by 0% to 100%, and the timing at which the R wave appears in the electrocardiogram waveform is considered to be 0%. Since the amplitude level of the R wave among the waves in the electrocardiogram is the maximum, the time position of the R wave is considered as a reference position of the heartbeat phase. Here, a position expressed by the heartbeat phase of 0% to 100% is referred to as a "phase positions".

As illustrated in FIG. 4, the electrocardiogram waveform or the heartbeat shape varies time to time. In this case, the length of a period (R-R interval, R-R interval') until a subsequent R wave appears after the R wave appears, that is, the cardiac cycle, varies. In this case, when the electrocardiogram waveform is acquired at different timings before and after surgery, waveforms having different cardiac cycles can be acquired. When the cardiac cycle varies, a real time (actual time) of an activity occurs in the repetitive heartbeats, particularly, the actual time from the R wave differs even at the same heartbeat phase.

When the cardiac cycle varies, intervals of the actual time positions (actual time intervals) in the cardiac cycle also varies. Therefore, a range in which the actual time intervals easily vary and a range in which the actual time intervals hardly vary are present in the cardiac cycle. This is because even when the heart rate varies, that is, even when the cardiac cycle varies, a simulation generated from the sinoatrial node is transmitted in the almost same time (when the electrical transmission system is normal). On the other hand, when the electrical transmission system is damaged or recovered, the time varies.

That is, the length of the actual time (also referred to as "PT time") of a section (also referred to as "PT section") from a start of the P wave and an end of the T wave in the continuous cardiac cycles has difficulty in variation. On the other hand, the length of the actual time (also referred to as "non-PT time") of a section (also-referred to as "non-PT section") from an end of the T wave and a start of the P wave in one cardiac cycle has easiness in variation.

The PT time is a total time of a time (also referred to as "PQ time") from a start of the P wave to the actual time position of the Q wave and a time (also referred to as "QT time") from the actual time position of the Q wave to an end of the T wave.

The CT device 200 captures an image at equal intervals (phase intervals) is an repetitive cardiac cycle. The CT device 200 may acquire 20 a volume data in synchronization with the heartbeat which is acquired from the electrocardiograph 300. In this case, it is possible to acquire volume data in which the phase of 5% step.

The images are captured 20 times per one cardiac cycle as an example, but the present disclosure is not limited to this configuration. The CT device 200 may capture an image at the heartbeat phases of 0%, 20%, 40%, 60%, and 80% (100% is equal to 0% and is thus omitted) and acquire volume data.

The CT device 200 cannot capture an image at 20 phases in one cardiac cycle without any change, because about 0.5 seconds is required for one turn of a detector. Accordingly, the CT device 200 acquires an electrocardiogram while rotating the detector, distributes a sinogram acquired at the time of 0% to reconstruct volume data at the heartbeat-phase of 0%, based on the heartbeat phase at which the sonogram is acquired, and distributes a sonogram acquired at the time of 20% to reconstruct volume data at the heartbeat phase of 20%. This is referred to as electrocardiogram synchronization imaging.

The medical image processing device 100 can express and display the shape of the heartbeat by acquiring volume data at the heartbeat phases which are captured by the CT device 200 and continuously reproducing three-dimensional images which are acquired from the volume data at the heartbeat phases Volume Data Arranging Method An image arranging method for observing a heartbeat will be described below.

Figure 5:
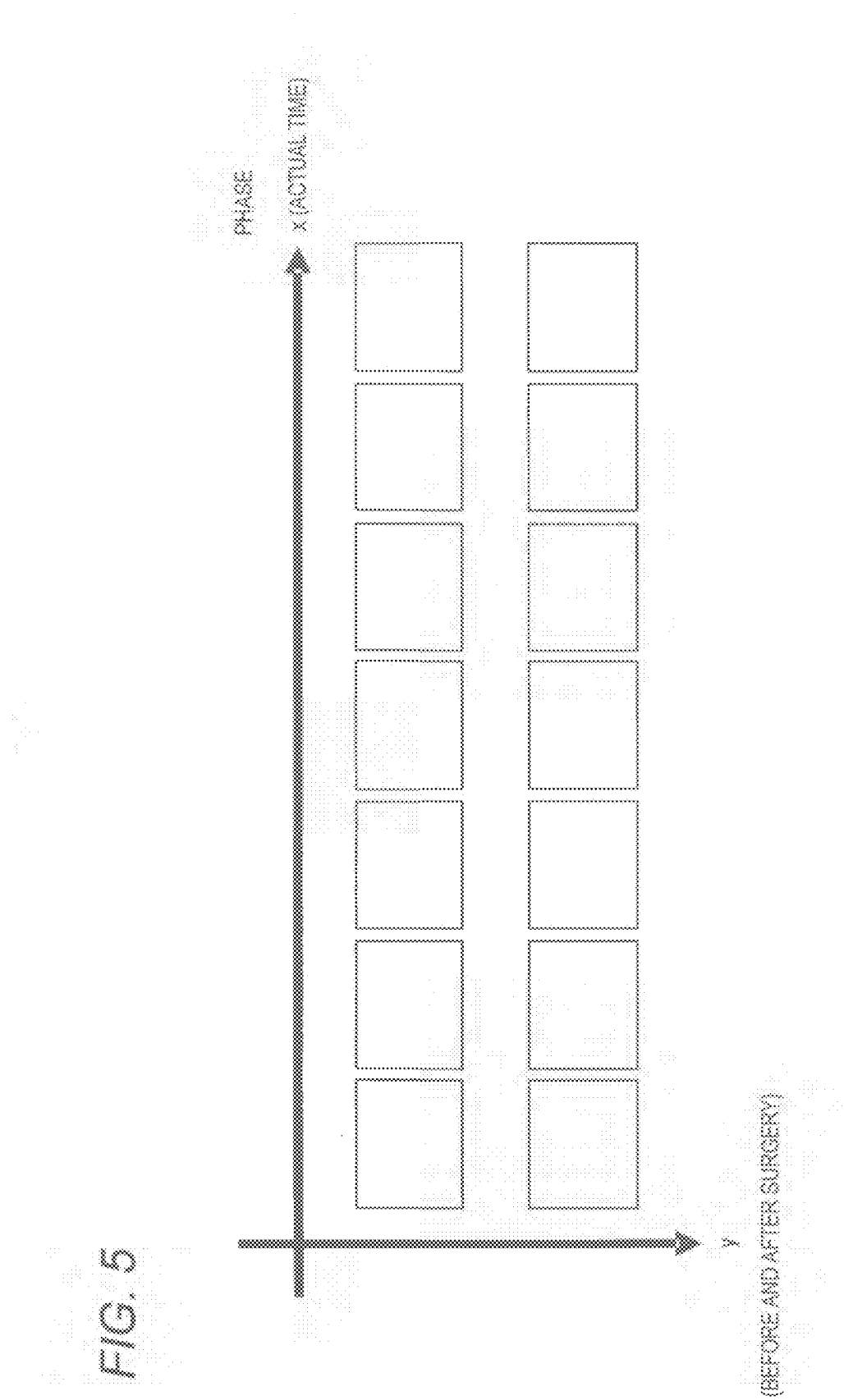
FIG. 5 is a schematic diagram illustrating an array example of volume data in each of heartbeat phases.

FIG. 5 is a schematic diagram illustrating an array example of volume data at the heartbeat phases. In FIG. 5, a time axis x and a time axis y are used, the time axis x being defined by phase positions of heartbeat phases and the time axis y being defined by time intervals of the time corresponding to the treatment progress before or after surgery are used. The time interval defined by the time axis x may be 5%. The time interval defined by the time axis y may be, for example, one week, one month, or a half year for observation of the progress.

The processor 140 classifies volume data acquired from the CT device 200 depending on whether the volume data is preoperative data or postoperative data and generates plural image groups. Here, as the result of classification, a preoperative image group and a postoperative image group are formed.

The processor 140 arranges the preoperative volume data along the time axis x in the order of heartbeat phases. Similarly, the processor 140 arranges the postoperative data along the time axis x in the order of heartbeat phases. The volume data may not be arranged actually (in an actual space) and the array order may be determined based on the imaging time of the volume data or the like.

In this way, the processor 140 arranges: the volume data, on the coordinate plane in consideration of the short-term lapse of time such as the heartbeat phase and the long-term lapse of time such as before and after surgery. Since the heartbeat phases often have periodicity, the volume data can be compared at the same heartbeat phase before and after surgery.

The periodicity of the phases may not be strict. A repetitive motion of rotating a shoulder may be considered as a motion which periodically changes with the short-term lapse of time (a motion having a phase).

When the change with the short-term lapse of time and the change with the long-term lapse of time are arranged in one time axis and are observed, it is difficult to compare plural shapes of motions corresponding to short-term time positions. On the other hand, when the time is extended two-dimensionally and the volume data are arranged as illustrated in FIG. 5, comparison and verification are facilitated.

Adjustment of Phase interval and Interpolation of Phase

Figure 6:
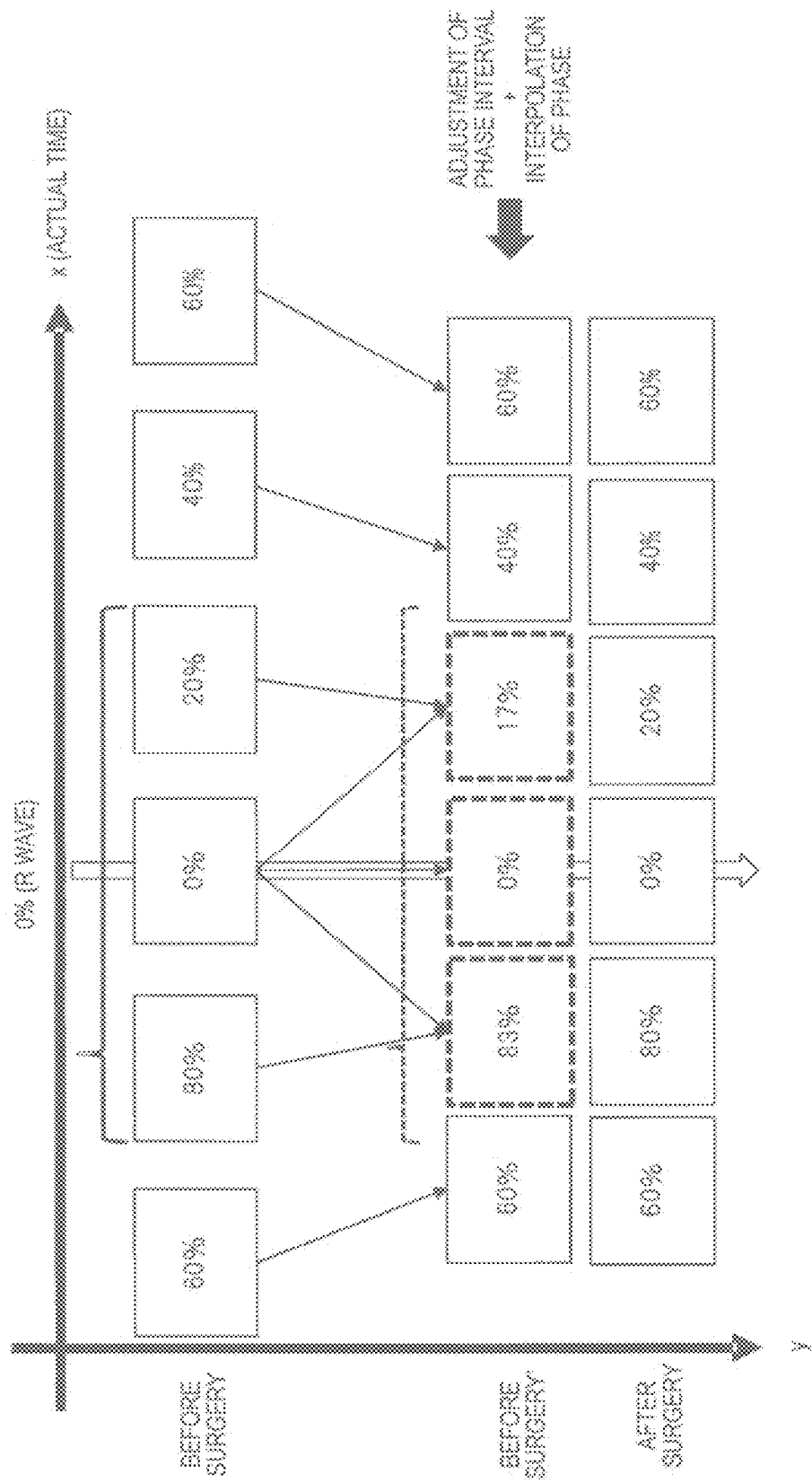
FIG. 6 is a schematic diagram illustrating an adjustment example of a phase intervals before and after surgery.

FIG. 6 is a schematic diagram illustrating an adjustment example of a phase interval before and after surgery. In FIG. 6, the sections of 83% to 100% and 0% to 17% of the preoperative heartbeat phase are the PT sections.

In FIG. 6, the volume data are arranged at the heartbeat phases with an equal interval along the time axis x before and after surgery. In FIG. 6, the heartbeat phases with an equal interval are 0%, 20%, 40%, 60%, and 80%.

The processor 140 compares the volume data at the heartbeat phases (40% and 60% in FIG. 6) in the non-PT section without adjusting the phase interval before and after surgery. This is because a change rate in length of the actual time of the cardiac cycle before and after surgery is equal to a change rate of the actual time position corresponding to the phase positions in the non-PT section.

On the other hand, the processor 140 compares the volume data at the heartbeat phases (0%, 20%, and 80% in FIG. 6) in the PT section with the phase interval adjusted before and after surgery. In the example illustrated in the drawing, the time taken from 0%, to 20% after surgery corresponds to the time taken from 0% to 17% before surgery.

When the phase interval is adjusted, the processor 140 generates interpolated volume data at an interpolation position corresponding to the postoperative phase position, based on the plurality of preoperative volume data at the heartbeat phases (0%, 20%, and 80% in FIG. 6) in the PT section. The processor 140 derives the interpolation position based on the actual time length of the preoperative cardiac cycle, the actual time length of the postoperative cardiac cycle, the actual time length of the RT section, and the postoperative phase position which is compared with the interpolated volume data. The derivation may include calculation.

The processor 140 performs motion analysis based on pixel values of the plurality of volume data and acquires information of the motion analysis. The processor 140 generates interpolated volume data at the interpolation position which is located between plural phase positions, based on the acquired information of the motion analysis. The method of generating the interpolated volume data is known and a method described in US 2011/0075888 A may be used.

Accordingly, the medical image processing device 100 can acquire the volume data at the phase positions which could not be acquired from the CT device 200 to follow she heartbeat. As a result, a user can observe a smoother heartbeat course.

In FIG. 6, the processor 140 generates interpolated volume data at the interpolation position corresponding to the phase position of 83% before surgery, based in the volume data at the phase position of 80% before surgery and the volume data at the phase position of 100% (0%) before surgery. The interpolated volume data is considered as a comparison target of the volume data at the phase position of 80% after surgery. The processor 140 generates a three-dimensional image (interpolated image) at the interpolation position fem the interpolated volume data.

The processor 140 generates interpolated volume data at the interpolation position corresponding to the phase position of 17% before surgery, based on the volume data at the phase position of 0% before surgery and the volume data at the phase position of 20% before surgery. This interpolated volume data is considered as a comparison target with the volume data at the phase position of 20% after surgery. The processor 140 generates a three-dimensional image (interpolated image) at the interpolation position from the interpolated volume data.

The actual time length (that is, the preoperative PT time) between the phase position of 83% and the phase position of 17% before surgery is equal to the actual time length (that is, the postoperative PT time) between the phase position of 80% and the phase position of 20% after surgery. That is, in the PT section, even when the phase interval (relative time interval) is changed depending on the actual time length of the cardiac cycle, the actual time interval is not changed.

In this way, the processor 140 maintains the PT time and adjusts the phase interval before and after surgery. The processor 140 interpolates the phase (generates the interpolated volume data at the interpolation position) so as to easily compare three-dimensional images before and after surgery.

The processor 140 correlates the volume data before and after surgery as comparison targets with priority given to the actual time in the PT section and priority given to the heartbeat phase in the non-PT section at the time of adjustment of the phase interval. Accordingly, the processor 140 adjusts the phase interval nonlinearly (irregularly) for each phase position in the cardiac cycle. Accordingly, a user can compare and observe the heart shape based on the phase-adjusted volume data depending on physiological stages of the heartbeat using the medical image processing device 100.

In this example, the CT device 200 operates in synchronization with the electrocardiograph 300 and acquires the volume data at a predetermined heartbeat phase, but the medical image processing device 100 may not acquire the output result of the electrocardiograph 300. In this case, the processor 140 of the medical image processing device 100 may estimate a predetermined actual time range before and after the phase position of 0% as the PT time. The predetermined actual time range may be designated by the UI 120.

When the QT time in the cardiac cycle is long, the phase range of the T wave and the phase range of the P wave may overlap. In this case, the processor 140 may maintain the PQ time and may not maintain the QT time, or may maintain the QT time and may not maintain the PQ time. By maintaining the PQ time, the medical image processing device 100 can facilitate the observation of a motion of an atrium. By maintaining the QT time, the medical image processing device 100 can facilitate observation of a motion of a ventricle.

When an observation target is a heart into which a pacemaker is inserted, necessity of observation of the motion of an atrium and the P wave decreases. Accordingly, the processor 140 may maintain the QT time may not maintain the PQ time. The same is applied to a case in winch the P wave is not sinus rhythm.

Operation of Medical Image Processing Device

As operation example of the medical image processing device 100 will be described below.

Figure 7:
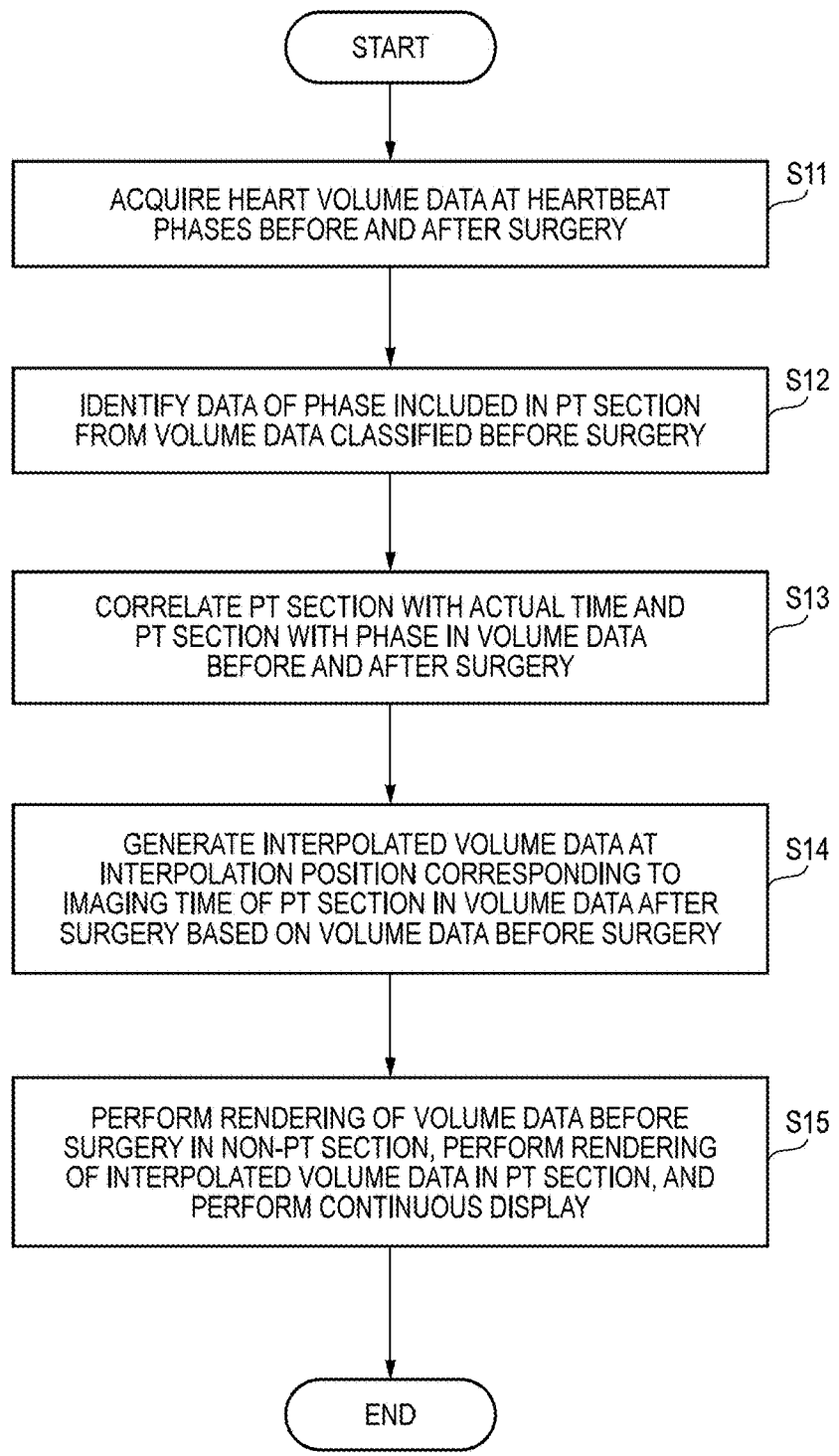
FIG. 7 is a flowchart illustrating an operation example of a medical image processing device.

FIG. 7 is a flowchart illustrating the operation example of the medical image processing device 100.

First, the port 110 acquires plurality of volume data from the CT device 200 (S11) and stores the acquired volume data in the memory 150.

The processor 140 classifies the plurality of volume data into preoperative volume data and postoperative volume data. The processor 140 identifies the volume data included in the PT section from the volume data classified as the preoperative volume data (S12).

The following method can be thought as the method of designating the PT section in the cardiac cycle. The processor 140 may extract information of the PT section from the electrocardiogram data acquired by the port 110. The medical image processing device 100 does not cooperate with the electrocardiograph 300 and a user may input information of the PT section via the UI 120 while watching the electrocardiogram waveform acquired in advance by the electrocardiograph 300. The user may arbitrarily input a predetermined period including the R wave of the electrocardiogram waveform as the PT section via the UI 120.

The processor 140 correlates the preoperative volume data and the postoperative volume data with each other in real time in the PT section and at the heartbeat phase in the non-PT section (S13). In S13, the processor 140 does not change the postoperative phase interval but adjusts the preoperative phase interval.

The processor 140 generates interpolated volume data at an interpolation position based on the plurality of preoperative volume data (S14). The interpolation position is a preoperative phase position of which the phase interval is adjusted and which is correlated with a postoperative phase position. In FIG. 6, the interpolation positions are the phase positions of 83% and 17% before surgery.

Before surgery, the processor 140 generates a three-dimensional image by rendering the preoperative volume data in the PT section and generates a three-dimensional image by rendering the interpolated volume data in the non-PT section. After surgery, the processor 140 generates a three-dimensional image by rendering the postoperative volume data in the PT section and the non-PT section. The processor 140 continuously displays the generated three-dimensional images on the display 130 (S15).

The following method can be thought as a display mode of the three-dimensional images.

The processor 140 may arrange the preoperative image group and the postoperative image group and display the arranged image groups on the display 130. That is, the processor 140 may arrange and display the plural preoperative three-dimensional images and the plural postoperative three-dimensional images in time series in correlation with each other. As a result, the three-dimensional images are displayed on the display 130 is the array illustrated in FIG. 6.

The processor 140 may perform combination of the correlated images with the three-dimensional images included in the preoperative image group and the three-dimensional images included in the postoperative image group and display the combined images on the display 130. Here, the correlated images are the three-dimensional images at the phase position of 60% before surgery and the three-dimensional images at the phase position of 60% after surgery. This is because the phase positions are in the non-PT section. The correlated images are the three-dimensional images at the phase position of before surgery and the three-dimensional images at the phase position of 80% after surgery. This is because the phase positions are in the PT section. Examples of the combined image include a difference image, an alpha-blended image, and various other images.

The processor 140 may display information on a distortion amount of the correlated volume data on the display 130 with the volume data included in the preoperative image group and the volume data included in the postoperative image group.

Here, the distortion amount refers to a distortion amount derived from the time-series volume data before and after. For example, the processor 140 may register the volume data before and after and set a strain tensor as the distortion amount based on a variation of a tissue. A maximum principal strain, a shearing strain, or a minimum principal strain may be used as the strain, or a combined value thereof may be used.

The processor 140 may add colors to a ray-cast image of the volume data depending on the strain tensor. Accordingly, the shape and the dynamic state of the tissue can be easily grasped. The processor 140 may repetitively display the volume data included in the image groups.

The processor 140 may derive a single volume data from the image group and visualize the derived volume data as a still image. For example, it can be considered that the processor 140 correlates the positional relationships of all the volume data in the image group by registration and visualizes the total sum of movements over all the phases and the maximum speed over all the phases. The processor 140 may combine the single volume data derived from the preoperative image group and the single volume data derived from the postoperative image group to generate a single volume data and may visualize the generated single volume data.

Effects and the Like

Figure 8:
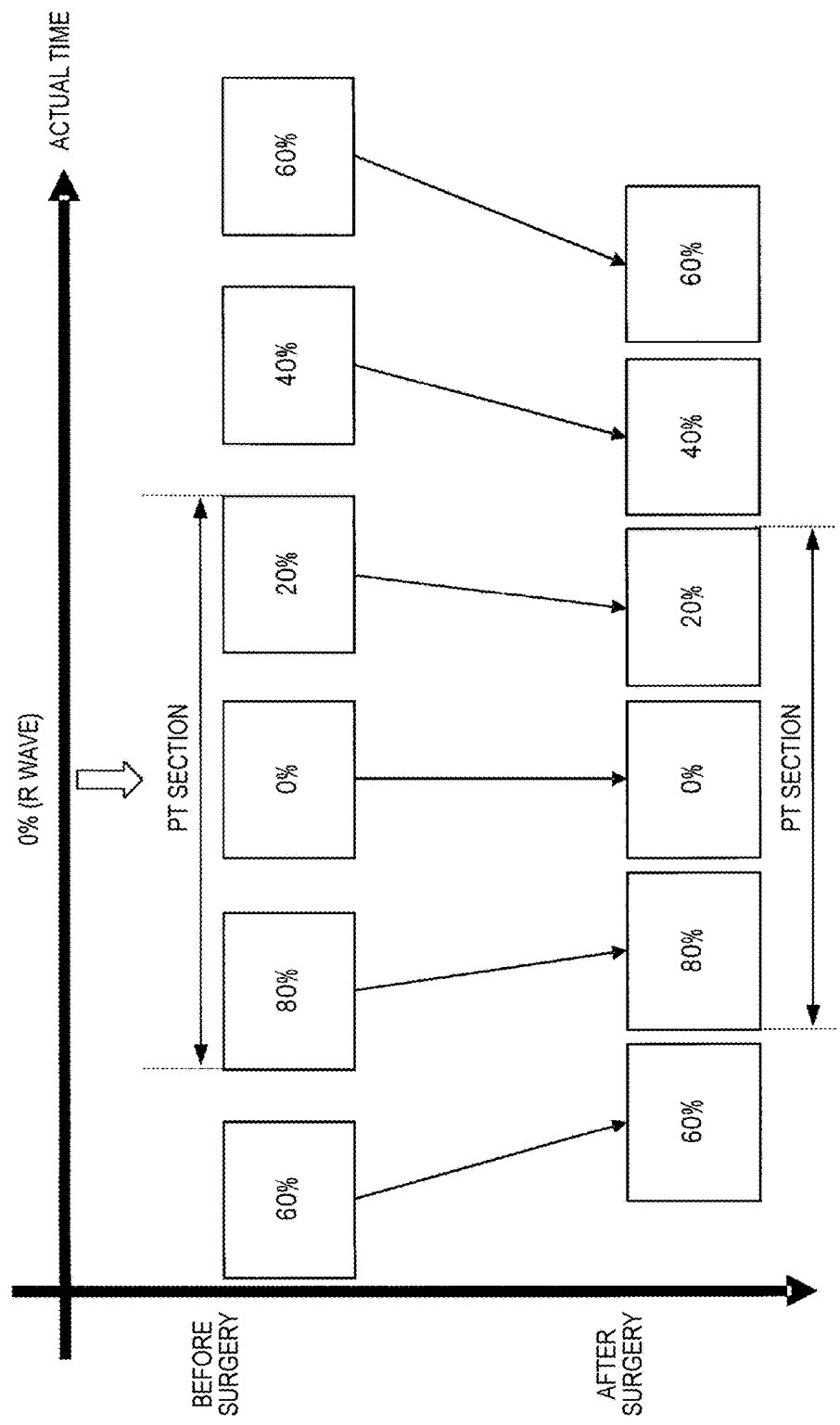
FIG. 8 is a schematic diagram illustrating adjustment of a phase interval according to a comparative example.

FIG. 8 is a schematic diagram illustrating adjustment of a phase interval in a comparative example. In the comparative example, the medical image processing device correlates the volume data at the same phase position before, and after surgery. When the cardiac cycles before and after are different from each other, the actual time length of the cardiac cycle before surgery is different from the actual time length of the cardiac cycle after surgery. Accordingly, the correlation is performed such that the actual time length of the cardiac cycle before surgery varies over the entire phases. Therefore even when the volume data are based on the same phase positions, the physiological stages of the heartbeats do not correspond to each other. Accordingly, different movements of a cardiac wall before and after surgery ate observed and it is difficult to accurately compare the movement timings of the cardiac wall before and after surgery.

On the other hand, before and after surgery, the medical image processing device 100 according to this embodiment maintains the actual time in the PT section in which the actual time length is not hardly changed, maintains the heartbeat phases in the non-PT section in which the actual time length of the cardiac cycle is easily changed, and correlates the time positions. Accordingly, in the medical image processing device 100, the physiological stages of the heartbeats before and after surgery match each other and it is possible to accurately compare and display the movement timings of the cardiac wall.

The medical image processing device 100 can improve accuracy of correlation of the physiological stages of the heartbeats before and after surgery and can clarify a difference due to fine movement of a heart before and after surgery. Accordingly, a user can compare and observe the shapes of a heart before and after surgery and can easily confirm improvement of a heart disease after surgery. Examples of the heart disease include a trouble of a heart valve, plugging of a blood vessel, or a trouble in an electrical motion of the heart.

According to the medical image processing device 100, in comparison with observation of a motion of a heart using the electrocardiogram, since the motions of a heart before and after surgery can be compared and displayed in nonlinear correlation, it is possible to easily acquire derailed information of a heart disease. According to the medical image processing device 100, in comparison with observation of a motion of a heart using the EPS, it is possible to reduce invasion of a human body and to reduce a patient's burden. In this way, according to the medical image processing device 100, it is possible to achieve both the ease of examination using the electrocardiograph 300 and the precision of examination using the EPS.

A user may use the medical image processing device 100 alone for the purpose of examination, diagnosis, or treatment of a heart disease or may use another medical instrument along with the medical image processing device 100. In this case, at least one of electrocardiogram analysis using the electrocardiograph 300, catheter examination (EPS) using a catheter, and catheter treatment (ablation) using a catheter is performed in addition to the image diagnosis using the medical image processing device 100. When there is a heart disease, embedment of a cardiac pacemaker may be performed instead of the catheter treatment or in addition to the catheter treatment. Particularly, the medical image processing device can be usefully used for prognosis analysis of a patient subjected to ablation surgery from the EPS.

The follow flow can be considered for examination and treatment of a heart disease using the medical image processing device 100. First, a user acquires and analyzes an electrocardiogram using the electrocardiograph 300, compares and verifies corresponding images using the medical image processing device 100, and makes an imaging diagnosis. This use of the medical image processing device 100 is a preoperative use. When the heart is recognized to be abnormal as the result of electrocardiogram analysts or imaging diagnosis, the user performs catheter examination using a catheter and performs catheter treatment or embedment of a pacemaker if necessary. The user acquires again analyzes an electrocardiogram using the electrocardiograph 300, compares and verifies corresponding images using the medical image processing device 100, and performs imaging diagnosis. This use of the medical image processing device 100 is a postoperative use.

In this flow, by using the medical image processing device 100 before surgery, the user can improve reading accuracy of a heart disease in an examination step, improve a discovery rate of a heart disease, and determine an appropriate treatment plan after the examination. By using the medical image processing device 100 after surgery, the user can improve reading accuracy of a heart disease state in a step after treatment and easily diagnose improvement of a heart disease.

In the present disclosure, a medical imaging device includes at least one imaging unit and at least one processor and generates a plurality of image data at a plurality of imaging times. The imaging times includes a first time component which is defined by a first time interval and a second time component which is defined by a second time interval being shorter than the first time interval. The processor determines, based on both an actual time of the second time component and a time ratio of the second time component, according to a plurality of two-dimensional or three-dimensional first image data of a living body, the second time component of the plurality of second image data in correlation with the second time component of the plurality of first image data. The imaging unit images an image of the living body and acquires imaging data at the imaging times including the determined second time component determined by the processor. The processor generates the plurality of two-dimensional or three-dimensional second image data based on the imaging data imaged by the imaging unit.

Second Embodiment

In the first embodiment, the CT device 200 captures the image at constant phase intervals and acquires a plurality of volume data, and the medical image processing device 100 acquires a volume data and adjusts the phase Interval of some volume data. In a second embodiment, a CT device 200A captures an image in a state where some phase intervals ate adjusted and acquires a plurality of volume data.

A medical image processing device 100A according to this embodiment is the same configuration as the medical image processing device 100 according to the first embodiment and thus description thereof will not be repeated. In this embodiment, the CT device 200A has the function of nonlinearly adjusting the phase interval in consideration of the actual time and the heartbeat phase in the medical image processing device 100 according to the first embodiment.

Figure 9:
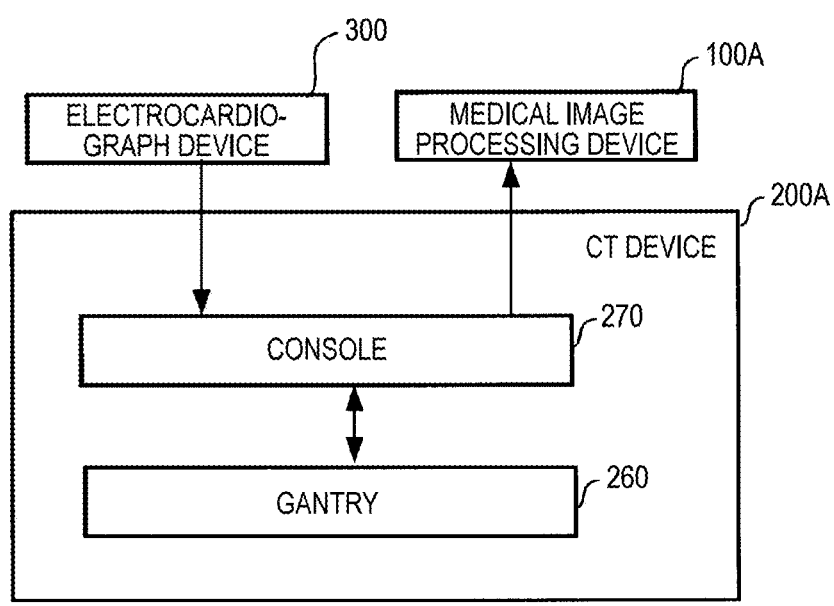
FIG. 9 is a block diagram illustrating a configuration example of a CT device according to a second embodiment

FIG. 9 is a block diagram illustrating a configuration example of the CT device 200A. The CT device 200A includes a gantry 260 and a console 270.

The gantry 260 includes an X-ray generator and an X-ray detector. The gantry 260 detects X-rays transmitted through a human body and acquires X-ray detection data by capturing an image at a predetermined timing instructed by the console 270.

The console 270 includes a port, a UI, a display, a processor, and a memory. The console 270 is connected to the medical image processing device 100A and the electrocardiograph 300. The console 270 acquires electrocardiogram data from the electrocardiograph 300. The console 270 acquires a plurality of X-ray detection data from the gantry 260 and generates volume data based on the C-ray detection data. The console 270 transmits the generated volume data to the medical image processing device 100A.

The console 270 controls an imaging timing of the gantry 260. In this case, the console 270 acquires information of an actual time length of one cardiac cycle and an actual time length of a PT sec lion based on an electrocardiogram waveform which is acquired from the electrocardiograph 300.

The gantry 260 captures an. image at predetermined heartbeat phases before and after surgery. At this time, the console 270 correlates the imaging timings before and after surgery with the actual time in the PT section and the heartbeat phase in the non-PT section and sends the correlation information to the gantry 260.

Figure 10:
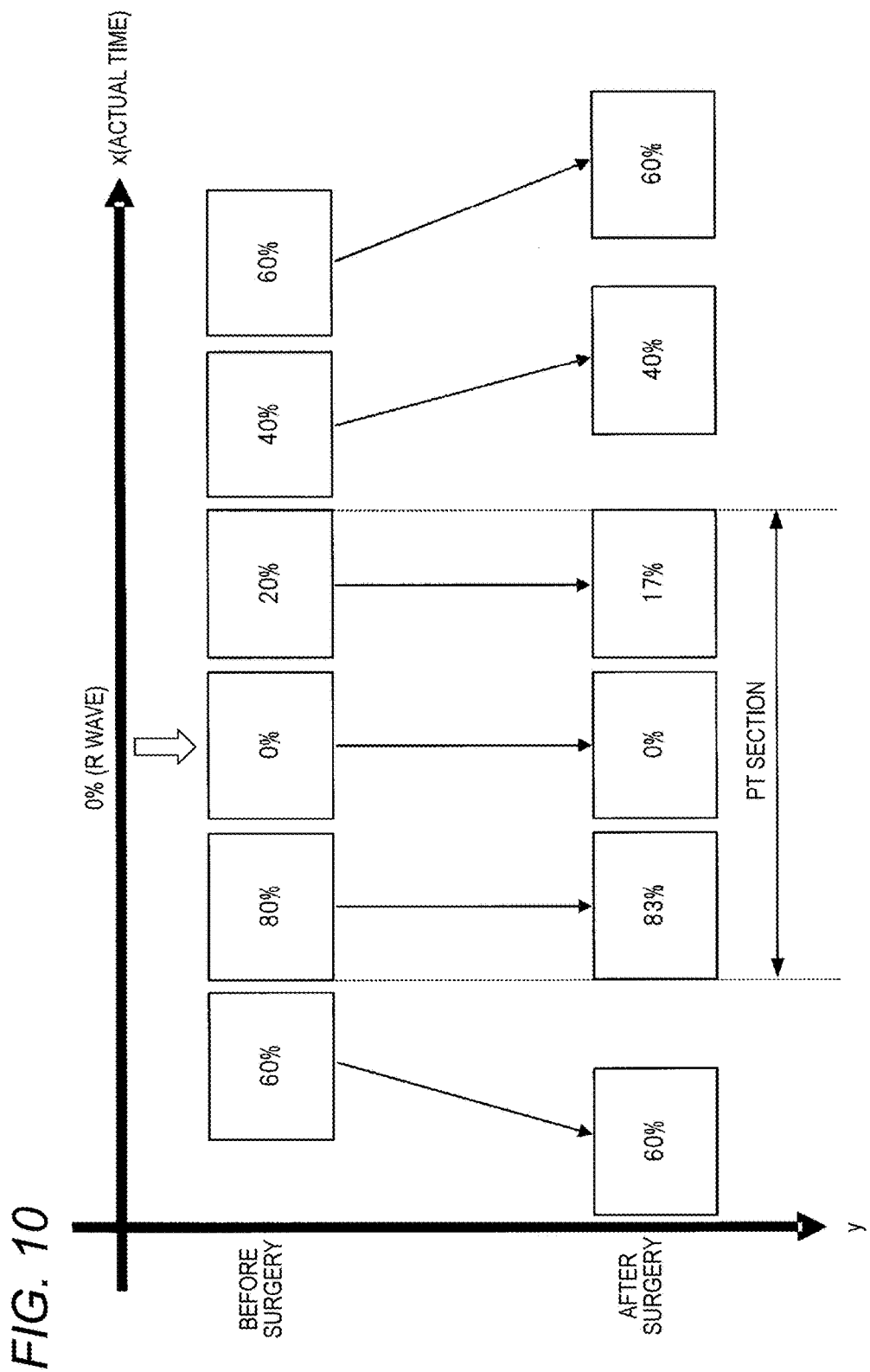
FIG. 10 is a schematic diagram illustrating an adjustment example of an imaging timing before and after surgery.

FIG. 10 is a schematic diagram illustrating an example in which the imaging timings of the CT device 200A before and after surgery are correlated. In FIG. 10, before surgery, it is assumed that the gantry 260 captures an image at heartbeat phases of 0%, 20%. 40%, 60%, and 80% and the console 270 stores volume data in the memory. The image capture at the heartbeat phases is an example and the image may be captured at other heartbeat phases. The preoperative phase positions of 80% to 100% and 0% to 20% are defined as the PT section.

The console 270 acquires postoperative electrocardiogram data from the electrocardiograph 300. The console 270 already acquires preoperative electrocardiogram data from the electrocardiograph 300 and stores the acquired data in the memory.

The console 270 acquires information of the actual time length of a preoperative cardiac cycle from the preoperative electrocardiogram data. The console 270 acquires information of the actual time length of a postoperative cardiac cycle from the postoperative electrocardiogram data. The console 270 acquires information of the actual time length of the PT section front preoperative or postoperative electrocardiogram waveform data.

The console 270 calculates the postoperative imaging timings corresponding to the preoperative image capture timings based on the actual time length of the preoperative cardiac cycle, the actual time length of the postoperative cardiac cycle, and the actual time length of the PT section. In this case, the console 270 correlates the preoperative and postoperative imaging timings based on the actual time in the PT section and the heartbeat phase in the non-PT section.

As the correlation result, in FIG. 10, when the preoperative phase position of 60% is set as an imaging timing, the postoperative imaging timing is the phase position of 60%. When the preoperative phase position of 80% is set as an imaging timing, the postoperative imaging timing is the phase position of 83%. When the preoperative phase position of 0% is set as an imaging timing, the postoperative imaging timing is the phase position of 0%. When the preoperative phase position of 20% is set as an imaging timing, the postoperative imaging timing is the phase position of 17%. When the preoperative phase position of 40% is set as an imaging timing, the postoperative imaging timing is the phase position of 40%.

The console 270 sends information of the postoperative imaging timings correlated with the preoperative imaging timings to the gantry 260. The gantry 260 captures an image at the postoperative imaging timings which are acquired from the console 270 and acquires X-ray detection data. The console 270 generates volume data from the X-ray detection data from the gantry 260 and transmits the generated volume data to the medical image processing device 100A.

In this way. the CT device 200A acquires informal ion of the preoperative and postoperative cardiac cycles and the actual time length of the PT section and determines the postoperative imaging timing based on the preoperative and postoperative cardiac cycles and the actual time length of the PT section. Accordingly, the CT device 200A can nonlinearly correlate the preoperative imaging timings and the postoperative imaging timings. Therefore, a user can easily compared and observe the shape of the heart before and after surgery depending on the physiological stage of the heartbeat.

The medical image processing device 100A acquires the volume data which is acquired by capturing an image in a state in which the imaging timings are adjusted from the CT device 200A. Accordingly, in comparison with the case in which the phase interval adjustment and the phase interpolation are performed before and after surgery as in the first embodiment, the medical image processing device 100A can reduce a processing load of nonlinearly correlating the preoperative volume data and the postoperative volume data. The medical image processing device 100A can reduce a processing load of generating interpolated volume data at a timing (interpolation position) at which an image is not actually captured and can easily compare and verify the heartbeat before and after surgery.

The CT device 200A may newly reconstruct the volume data from positions corresponding to the phase position of the preoperative interpolation position in the sonogram and transmit the reconstructed volume data to the medical image processing device 100A. In this example (the example illustrated in FIG. 10), the volume data at the phase positions of 83% and 17% are acquired from the sonograms of the phase positions of 83% and 17%. The CT device 200A may transmit the sonograms to the medical image processing device 100A and the medical image processing device 100A may reconstruct the volume data.

Other Embodiments

The present disclosure is not limited to the above-mentioned configurations of the embodiments, but may employ any configuration as long as the functions described in the appended claims or the functions of the configuration of this embodiment can be achieved.

In the above-mentioned embodiment, the heartbeat is exemplified as a change example with the short-term lapse of time and the preoperative and postoperative states are exemplified as a change example with the long-term lapse of time, but the present disclose is not limited thereto. As another change example with the short-term or long-term lapse of time, the course of respiration, movement of a joint (such as a motion of rotating a shoulder), the progress of a tumor, contrast radiography and non-contrast radiography, a difference in imaging condition of the CT dev ice 200, and sleeping and non-sleeping states can be considered. The contrast radiography and non-contrast radiography refers to an imaging of the CT device 200 in a state in which a contrast medium is injected into the body and an imaging of the CT device 200 in a state in which a contrast medium is not injected into the body.

A motion of rotating another part of a human body (such as a hand, a foot, a waist, a shoulder, or a neck) other than the shoulder may be observed. In this case, data of the part to be observed is extracted from the volume data and a three-dimensional image is generated.

As the change with the short-term lapse of time and the change with the long-term lapse of time, two changes can be arbitrarily selected from the above-mentioned change examples. The heartbeat phase in inhalation and the heartbeat phase in exhalation may be combined and the volume data may be arranged on a coordinate plane defined by the time axis x and the time axis y.

It is preferable that the heartbeat phase, the course of respiration, and the motion of a joint be considered as changes with the short-term lapse of time. It is preferable that the progress of a tumor, the preoperative and postoperative states, the contrast radiography and non-contrast radiography, the difference in other imaging conditions, and the sleeping and non-sleeping states be considered as changes with the long-term lapse of time. The change with the short-term lapse of time may accompany a periodic change, that is, a repetitive motion. In this case, the short-term lapse of time corresponds to the relative time (phase) to one cycle.

In the above-mentioned embodiment, the medical image processing device 100 generates and compares the interpolated volume data at an interpolation position corresponding to a predetermined postoperative timing, based on the preoperative volume data. The medical image processing device 100 may generate and compare interpolated volume data at an interpolation position corresponding to a predetermined preoperative timing, based on the postoperative volume data.

In the above-mentioned embodiment, the medical image processing device 100 acquires a plurality of volume data (three-dimensional image data) as image data from the CT device 200, arranges the plurality of volume data on the coordinate plane, and performs the correlation. The medical image processing device 100 may acquire two-dimensional image data as image data, arrange the two-dimensional image data on the coordinate plane, and perform the correlation. The two-dimensional image data may be data of a single fault imaged by the CT device 200 or another imaging device.

In comparison with the case in which the three-dimensional image data is used, it is possible to improve a time resolution by using the two-dimensional image data. Accordingly, the medical image processing device 100 can more easily compare images of a deformable object acquired at different timings with the same phase and improve comparison and verification accuracy. This is particularly effective for a magnetic resonance imaging (MRI) device.

In the above-mentioned embodiment, after the volume data are arranged and correlated, the three-dimensional images are generated from the volume data and the three-dimensional images are displayed. After the volume data ate arranged and the three-dimensional images are generated from the volume data, the three-dimensional images may be correlated and displayed. After the three-dimensional images are generated from the volume data, the three-dimensional images may be arranged, correlated, and displayed.

In the above-mentioned embodiment, the human body is exemplified as the living body, but an animal body may be used.

In the above-mentioned embodiment, when valve replacement of an aortic valve is performed as treatment of a heart, it is expected to improve movement of a mitral valve. The aortic valve and the mitral valve perform opening and closing operations similarly, but are different from each other in the moving timing or the moving period of one motion. Accordingly, the change of the aortic valve and the change of the mitral valve may be employed as the change with the short-term lapse of time and the change with the long-term lapse of time.

The aortic valve and the mitral valve are examples of a valve in the body, and the medical image processing device 100 may derive information of an interaction between plural other valves by comparison of preoperative images and postoperative images.

The above-mentioned embodiment may be used for comparison and verification of movement of a cardiac wall before and after surgery of embedding a pacemaker.

In the above-mentioned embodiment, the medical image processing device 100 or 100A and the CT device 200 or 200A can be used for comparison and verification of movement of a cardiac wall before and after treatment of a coronary disease. Particularly, it is possible to verify a region which is expected to be recovered and a region which is actually recovered in a coronary artery subjected to treatment.

In the above-mentioned embodiment, the medical image processing device 100 or 100A and the CT device 200 or 200A can be used for comparison and verification of movement of a cardiac wall before and after treatment of a stimulation transmission system. Particularly, stimulation is transmitted at a speed higher than an imaging speed of the CT device and comparison with physiological stages of a heartbeat matched is effective for determination of a treatment result.

In the above-mentioned embodiment, the volume data as a captured CT image is transmitted from the CT device 200 to the medical image processing device 100. Instead, in order to temporarily store the volume data, the volume data may be transmitted from the CT device 200 to a server over a network or the like and stored therein. In this case, the port 110 of the medical image processing device 100 may acquire the volume data via a wired line or a wireless line if necessary or may acquire the volume data via an arbitrary storage medium (not illustrated).

In the above-mentioned embodiment, the volume data as the captured CT image is transmitted from the CT device 200 to the medical image processing device 100 via the port 110. This includes a case in which the CT device 200 and the medical image processing device 100 are actually combined into one product. For example, this includes a case in which the medical image processing device 100 is handled, as a console of the CT device 200.

In the above-mentioned embodiment, an image is captured by the CT device 200 and volume data including information in the living body is generated, but an image may be captured by another device and volume data may be generated. Examples of another device include an MRI device, a positron emission tomography (PET) device, an angiography device, and other modality devices. The PET device may be used in combination with another modality device.

Summary of Embodiments of the Present Disclosure

A medical image processing device according to an embodiment of the present disclosure includes a port, a processor, and a display. The port acquires a plurality of two-dimensional or three-dimensional image data which are acquired from the same living body. The processor classifies the plurality of image data to generate plural image groups, based on a first time component which is defined by a first time interval among imaging times at which the plurality of image data are generated, and correlates the image data in the image groups based on both an actual time and a time ratio of a second time component which is defined by a second time interval shorter than the first time interval among the imaging times at which the plurality of image data are generated. The display displays images based on the plurality of image data based on the correlation of the image data in the image groups. The time ratio is, for example, a phase position.

According to this configuration, the medical image processing device nonlinearly correlates the image data in the plural image groups having different imaging times in consideration of both a time in which the living body easily strains and a time in which the living body hardly strains. Accordingly, the medical image processing device can facilitate comparison and observation of plural images in the plural image groups. Therefore, a user of the medical image processing device can easily confirm a long-term change of an observation target which strains in the short term. The long-term change may be improvement of the living body after surgery.

In the medical image processing device according to the embodiment of the present disclosure, the processor may correlate the image data in the image groups based on the actual time in a predetermined period according to the second time component which is included in an imaging period in which the plurality of image data included in the image group, and may correlate the image data in the image groups based on the time ratio to the imaging period in the period other than the predetermined period. The imaging period may be one cardiac cycle. The predetermined period may be a PT section.

According to this configuration, the medical image processing device can maintain the actual time in a predetermined period in which the living body is hardly deformable even when the imaging periods of the image groups are different from each other. Accordingly, the medical image processing device can prevent the images in the predetermined period in which the living body is hardly deformable from being distorted at the time of correlating the images in the image groups.

In the medical image processing device processing device according to the embodiment of the present disclosure, the image groups may include a first image group including a plurality of first image data and a second image group including a plurality of second image data. The processor may generate interpolated image data at a time position corresponding to the imaging time of the second image data, based on the plurality of first image data when the first image data correlated with the second image data is absent. The display may display an interpolated image based on the interpolated image data. The interpolated image data may be interpolated volume data.

According to this configuration, even when the time resolution of a medical imaging device generating the plurality of image data is relatively low, the medical image processing device can interpolate image data at an arbitrary time position based on the generated image data. Accordingly, when the image data are correlated between the plural image groups it is possible to interpolate the image data as a comparison target even when the image data of one side are not generated and are insufficient. As a result, a user of the medical image processing device can compare and verify the corresponding images in the plural image groups using the interpolated images and it is possible to improve diagnosis accuracy.

In the medical image processing device according to the embodiment of the present disclosure, the second time component may include a time having repetitive properties.

According to this configuration, the medical image processing device can display the images representing a repetitive motion, which are generated at different imaging times, in nonlinear correlation with each other. Accordingly, a user can compare and verify the repetitive motion at the different imaging times with high accuracy.

In the medical image processing device according to the embodiment of the present disclosure, the second time component may include a heartbeat phase.

According to this configuration, the medical image processing device can display the images representing a motion of a heart accompanied with a heartbeat, which are generated at different imaging times, in nonlinear correlation with each other. Accordingly, a user can compare and verify the motion of a heart accompanied with a heartbeat at the different imaging times with high accuracy.

In the medical image processing device according to the embodiment of the present disclosure, the port may acquire electrocardiographic information from an electrocardiograph. The processor may acquire information of a ventricular contraction time at which ventricular contraction appears from the electrocardiographic information and may set the ventricular contraction time as a reference point of the second time component. The ventricular contraction time may be a time at which an R wave is located.

According to this configuration, the medical image processing device can easily recognize the heartbeat phases in synchronization with the electrocardiograph.

In the medical image processing device according to the embodiment of the present disclosure, the first time component may include a preoperative time and a postoperative time before and after surgery of the living body.

According to this configuration, it is possible to compare and verify improvement of the living body before and after surgery.

In the medical image processing device according to the embodiment of the present disclosure, the display may arrange and display images based on the correlated image data in the image groups under the control of the processor.

According to this configuration, since a user can easily visually understand the correlation of the image between the plural image groups, it is possible to improve diagnosis accuracy.

In the medical image processing device according to the embodiment of the present disclosure, the processor may generate a combined image based on the correlated image data in the image groups. The display may display the combined image.

According to this configuration, a user can confirm the images corresponding to the second time component in the plural image groups through display of one combined image.

In the medical image processing device according to the embodiment of the present disclosure, the display may display information on the distortion amount of the correlated image data in the image groups under the control of the processor.

In the medical image processing device according to the embodiment of the present disclosure, the three-dimensional image data may be volume data of the living body.

According to this confirmation, the medical image processing device can display information on the display in a stereoscopic display mode corresponding to a user's intention. Accordingly, the user can instruct an appropriate display mode depending on types of a disease or a lesion and easily confirm the corresponding images in the plural image groups.

A medical imaging device according to another embodiment of the present disclosure includes an imaging unit and a processor and captures plural images at plural imaging times. The imaging times includes a first time component which is defined by a first time interval and a second time component which is defined by a second time interval shorter than the first time interval. The processor determines, based on both an actual time and a time ratio of the second time component according to a plurality of two-dimensional or three-dimensional first image data of the same living body, the second time components according to a plurality of second image data in correlation with the second time components according to the plurality of first image data. The imaging unit images the same living body and acquires imaging data at the imaging times including the determined second time components. The processor generates the plural two-dimensional or three-dimensional second image data based on the imaging data.

The medical imaging device may be the CT device 200A. The imaging unit may be the gantry 260. The processor may be included in the console 270. The first image data may be preoperative volume data. The second image data may be postoperative volume data. The imaging data may be X-ray detection data.

According to this configuration, the medical imaging device can nonlinearly correlate the image data in the plural image groups having different imaging times in consideration of both a time in which the living body is easily deformable and a time in which the living body is hardly deformable and generate image data. Accordingly, the medical imaging device can facilitate comparison and observation of plural images in the plural image groups. Therefore, a user of the medical imaging device can easily confirm a long-term change of an observation target which strains in the short term.

In the medical imaging device according to the embodiment of the present disclosure, the second time component may include a time having repetitive properties.

According to this configuration, the medical imaging device can capture the images representing a repetitive motion, which are generated at different imaging times, in nonlinear correlation with each other. Accordingly, a user can compare and verify the repetitive motion which is imaged at the different imaging times with high accuracy by confirming the captured images.

In the medical imaging device according to the embodiment of the present disclosure, the second time component may include a heartbeat phase.

According to this configuration, the medical imaging device can capture the images representing a motion of a heart accompanied with a heartbeat, which are generated at different imaging times, in nonlinear correlation with each other. Accordingly, a user can compare and verify the motion of a heart accompanied with a heartbeat which is imaged at the different imaging times with high accuracy by confirming the captured images.

In the medical imaging device according to the embodiment of the present disclosure, the first time component may include a preoperative time and a postoperative time before and after surgery of the living body.

According to this configuration, it is possible to compare and verify improvement of the living body before and after surgery.

A medical image processing method according to another embodiment of the present disclosure is a medical image processing method in a medical image processing device, and includes: acquiring a plurality of two-dimensional or three-dimensional image data which are acquired from the same living body; classifying the plurality of image data to generate plural image groups based on a first time component which is defined by a first time interval among imaging times at which the plurality of image data are generated; correlating the image data in the image groups based on both an actual time and a time ratio of a second time component which is defined by a second time interval shorter than the first time interval among the imaging times at which the plurality of image data are generated; and displaying images based on the plurality of image data based on the correlation of the image data in the image groups.

According to this method, the medical image processing device nonlinearly correlates the image data in the plural image groups having different imaging times in consideration of both a time in which the living body easily strains and a time in which the living body is hardly deformable. Accordingly, the medical image processing device can facilitate comparison and observation of plural images in the plural image groups. Therefore, a user of the medical image processing device can easily confirm a long-term change of an observation target which is deformable in the short term.

A medical imaging method according to another embodiment of the present disclosure is a medical imaging method in a medical imaging device generating a plurality of image data at plural imaging times, wherein the imaging times includes a first time component which is defined by a first time interval and a second time component which is defined by a second time interval shorter than the first time interval, and the medical imaging method includes: determining, based on both an actual time and a time ratio of the second time component, according to a plurality of two-dimensional or three-dimensional first image data of the same living body, the second time components according to a plurality of second image data in correlation with the second time components according to the plurality of first image data; imaging the same living body and acquiring imaging data at the imaging times including the determined second time components; and generating the plural two-dimensional or three-dimensional second image data based on the imaging data.

According to this method, the medical imaging device nonlinearly correlates the image data in the plural image groups having different imaging times in consideration of both a time in which the living body is easily deformable and a time in which the living body is hardly deformable, and can generate image data. Accordingly, the medical imaging device can facilitate comparison and observation of plural images in the plural image groups. Therefore, a user of the medical imaging device can easily confirm a long-term change of an observation target which is deformable in the short term.

A medical image processing program according to another embodiment of the present disclosure is a program causing a computer to perform steps of the above-mentioned medical image processing method.

According to this program, the medical image processing device executing the program nonlinearly correlates the image data in the plural image groups having different imaging times in consideration of both a time in which the living body is easily deformable and a time in which the living body is hardly deformable. Accordingly, the medical image processing device can facilitate comparison and observation of plural images in the plural image groups. Therefore, a user of the medical image processing device can easily confirm a long-term change of an observation target which is deformable in the short term A medical imaging program according to another embodiment of the present disclosure is a program causing a computer to perform steps of the above-mentioned medical imaging method.

According to this program, the medical imaging device executing the program nonlinearly can correlate the image data in the plural image groups having different imaging times in consideration of both a time in which the living body is easily deformable and a time in which the living body is hardly deformable, and can generate image data. Accordingly, the medical imaging device can facilitate comparison and observation of plural images in the plural image groups. Therefore, a user of the medical imaging device can easily confirm a long-term change of an observation target which is deformable in the short term.

The present disclosure is useful for a medical image processing device, a medical imaging device, a medical image processing method, a medical imaging method, and a medical image processing program which can easily confirm a long-term change of an observation target which is deformable in the short term.

What is claimed is:

1. A medical image processing device comprising a port, a processor and a display, wherein:
   the port acquires a plurality of two-dimensional or three-dimensional image data from a living body,
   the processor classifies the plurality of image data to generate a plurality of image groups based on a first time component,
   the first time component is defined by a first time interval among imaging times at which the plurality of image data are generated,
   the processor correlates each image data in one image group with each image data in another image group, based on both an actual time of a second time component and a time ratio of the second time component,
   the second time component is defined by a second time interval among the imaging times, and the second time interval is shorter than the first time interval,
   the processor correlates each image data in one image group with each image data in another image group based on the actual time of the second time component in a predetermined period within an imaging period,
   each image data of each image group is generated in the imaging period,
   the processor correlates each image data in one image group with each image data in another image group based on the time ratio of the second time component in another period within the imaging period other than the predetermined period, and
   the display displays images based on the plurality of image data based on the correlation of the image data in the image groups.

2. The medical image processing device according to claim 1,
   wherein the plurality of image groups include a first image group including a plurality of first image data and a second image group including a plurality of second image data,
   in a case where one of the first image data correlated with one of the second image data is absent, the processor generates interpolated image data at a time position corresponding to the imaging time of the one of second image data based on the plurality of first image data, and
   the display displays an interpolated images based on the interpolated image data.

3. The medical image processing device according to claim 1, wherein the second time component includes a time having repetitive properties.

4. The medical image processing device according to claim 3, wherein the second time component includes a heartbeat phase.

5. The medical image processing device according to claim 4,
   wherein the port acquires electrocardiographic information from an electrocardiograph, and
   the processor acquires information of a ventricular contraction time indicating ventricular contraction from the electrocardiographic information and sets the ventricular contraction time as a reference point of the second time component.

6. The medical image processing device according to claim 1, wherein the first time component includes a preoperative time before a surgery of the living body and a postoperative time after the surgery of the living body.

7. The medical image processing device according to claim 1, wherein the processor controls the display to arrange and to display images based on the correlated image data in each image group.

8. The medical image processing device according to claim 1,
wherein the processor generates a combined image based on the correlated image data in each image group, and the display displays the combined image.

9. The medical image processing device according to claim 1, wherein the processor controls the display to display information on a distortion amount of the correlated image data in each image group.

10. The medical image processing device according to claim 1, wherein the plurality of image data includes three-dimensional image data that includes volume data of the living body.

11. The medical image processing device according to claim 5, wherein said predetermined period within the imaging period includes at least time position of R wave.

12. A medical imaging device which includes an imaging unit and a processor and which generates a plurality of image data at a plurality of imaging times, wherein:
the imaging times includes a first time component which is defined by a first time interval and a second time component which is defined by a second time interval being shorter than the first time interval,
the processor determines, based on both an actual time of the second time component and a time ratio of the second time component, according to a plurality of two-dimensional or three-dimensional first image data of a living body, the second time component of the plurality of second image data in correlation with the second time component of the plurality of first image data,
the imaging unit images an image of the living body and acquires imaging data at the imaging times including the determined second time component,
the processor generates the plurality of two-dimensional or three-dimensional second image data based on the imaging data,
the processor correlates each image data in one image group with each image data in another image group based on the actual time of the second time component in a predetermined period within an imaging period,
each image data of each image group is generated in the imaging period, and
the processor correlates each image data in one image group with each image data in another image group based on the time ratio of the second time component in another period within the imaging period other than the predetermined period.

13. The medical imaging device according to claim 12, wherein the second time component includes a time having repetitive properties.

14. The medical imaging device according to claim 13, wherein the second time component includes a heartbeat phase.

15. The medical imaging device according to claim 12, wherein the first time component includes a preoperative time before a surgery of the living body and a postoperative time after the surgery of the living body.

16. The medical image device according to claim 14,
wherein the port acquires electrocardiographic information from an electrocardiograph, and
the processor acquires information of a ventricular contraction time indicating ventricular contraction from the electrocardiographic information and sets the ventricular contraction time as a reference point of the second time component.

17. The medical image device according to claim 16, wherein said predetermined period within the imaging period includes at least time position of R wave.

18. A medical image processing method of a medical image processing device, comprising:
acquiring a plurality of two-dimensional or three-dimensional image data from a living body;
classifying the plurality of image data to generate a plurality of image groups based on a first time component, wherein the first time component is defined by a first time interval among imaging times at which the plurality of image data are generated;
correlating each image data in one image group with each image data in another image group, based on both an actual time of a second time component and a time ratio of a second time component, wherein the second time component is defined by a second time interval among the imaging times, and the second time interval is shorter than the first time interval;
correlating each image data in one image group with each image data in another image group based on the actual time of the second time component in a predetermined period within an imaging period, wherein each image data of each image group is generated in the imaging period;
correlating each image data in one image group with each image data in another image group based on the time ratio of the second time component in another period within the imaging period other than the predetermined period; and
displaying images based on the plurality of image data based on the correlation of the image data in the image groups.

19. A medical imaging method of a medical imaging device generating a plurality of image data at a plurality of imaging times, wherein the imaging times includes a first time component which is defined by a first time interval and a second time component which is defined by a second time interval being shorter than the first time interval, the medical imaging method comprising:
determining, based on both an actual time of the second time component and a time ratio of the second time component, according to a plurality of two-dimensional or three-dimensional first image data of a living body, the second time component of the plurality of second image data in correlation with the second time component of the plurality of first image data;
imaging the living body and acquiring imaging data at the imaging times including the determined second time component;
generating the plurality of two-dimensional or three-dimensional second image data based on the imaging data;
correlating each image data in one image group with each image data in another image group based on the actual time of the second time component in a predetermined period within an imaging period, wherein each image data of each image group is generated in the imaging period; and
correlating each image data in one image group with each image data in another image group based on the time ratio of the second time component in another period within the imaging period other than the predetermined period.

* * * * *

UNITED STATES PATENT AND TRADEMARK OFFICE
CERTIFICATE OF CORRECTION

PATENT NO.          : 10,098,604 B2
APPLICATION NO.     : 15/277422
DATED               : October 16, 2018
INVENTOR(S)         : Kenichiro Yasuhiro It is certified that error appears in the above-identified patent and that said Letters Patent is hereby corrected as shown below:

On the Title Page

Abstract Line 5, "groups based OH" should read -- groups based on --

In the Specification

Column 1, Line 28, "2013/0231548 A)" should read -- 2013/0231548 A). --

Column 2, Line 28, "displacing" should read -- displaying --

Column 3, Line 47, "embodiment" should read -- embodiment. --

Column 5, Line 25, "The UT 120" should read -- The UI 120 --

Column 5, Line 37, "tendering" should read -- rendering --

Column 7, Line 9, "(phase intervals) is" should read -- (phase intervals) in --

Column 8, Line 32, "20%." should read -- 20%, --

Column 8, Line 60, "to follow she" should read -- to follow the --

Column 9, Line 5, "position fem" should read -- position from --

Column 9, Line 66, "case in winch" should read -- case in which --

Column 10, Line 2, "As operation" should read -- An operation --

Column 10, Line 67, "position of" should read -- position of 83% --

Signed and Sealed this
Nineteenth Day of February, 2019

Andrei Iancu
*Director of the United States Patent and Trademark Office*

CERTIFICATE OF CORRECTION (continued)
U.S. Pat. No. 10,098,604 B2

Column 11, Line 50, "after surgery ate" should read -- after surgery are --

Column 12, Line 11, "derailed" should read -- detailed --

Column 13, Line 21, "intervals ate" should read -- intervals are --

Column 13, Line 52, "sec lion" should read -- section --

Column 13, Line 55, "captures an." should read -- captures an --

Column 13, Line 65, "20%." should read -- 20%, --

Column 14, Line 15, "section front" should read -- section from --

Column 15, Line 31, "dev ice" should read -- device --

Column 16, Line 26, "data ate" should read -- data are --

Column 17, Line 20, "handled," should read -- handled --

Column 18, Line 15, "processing device processing device" should read -- processing device --